US00PP29783P2

(12) United States Plant Patent
Van Swieten

(10) Patent No.: US PP29,783 P2
(45) Date of Patent: Oct. 30, 2018

(54) ***PHALAENOPSIS* ORCHID PLANT NAMED 'PHALFEMYM'**

(50) Latin Name: ***Phalaenopsis* hybrid**
Varietal Denomination: PHALFEMYM

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/731,353

(22) Filed: Jun. 1, 2017

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALFEMYM', particularly characterized by having small, purple flowers with a red-purple lip, 1 to 3 peduncles that are medium long and sturdy, leaves that are oblong, and is propagated by meristem tissue culture, is disclosed.

3 Drawing Sheets

Genus and species: *Phalaenopsis* hybrid.
Variety denomination: 'PHALFEMYM'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFEMYM'.

The new *Phalaenopsis* plant is a product of a planned breeding program conducted by the inventor in Bleiswijk, The Netherlands. The objective of this breeding program was to create a new *Phalaenopsis* plant with numerous branches and many attractive and unique, small, purple flowers with a red-purple lip, suitable for potted plant production.

The new *Phalaenopsis* plant 'PHALFEMYM' is a result of cross-pollination made by the inventor in May 2006 in Bleiswijk, The Netherlands of the proprietary female, or seed parent, *Phalaenopsis* hybrid '01-1787' (unpatented) with the proprietary male, or pollen parent, *Phalaenopsis* hybrid '01-1712' (unpatented).

The new *Phalaenopsis* was selected by the inventor as a single plant within the progeny of the stated cross-pollination in a controlled greenhouse in Bleiswijk, The Netherlands in August 2009. Asexual reproduction of the new *Phalaenopsis* plant by meristem tissue culture since 2012 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 25, 2017. 'PHALFEMYM' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFEMYM' as a new and distinct variety of *Phalaenopsis* plant.

1) Small, purple flowers with a red-purple lip;
2) 1 to 3 peduncles;
3) Peduncle is medium long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in March 2017. Colors in the photographs may differ from the color values cited in the detailed botanical description, which accurately describe the actual colors of the new variety.

DESCRIPTION OF THE NEW VARIETY

Figure 1:
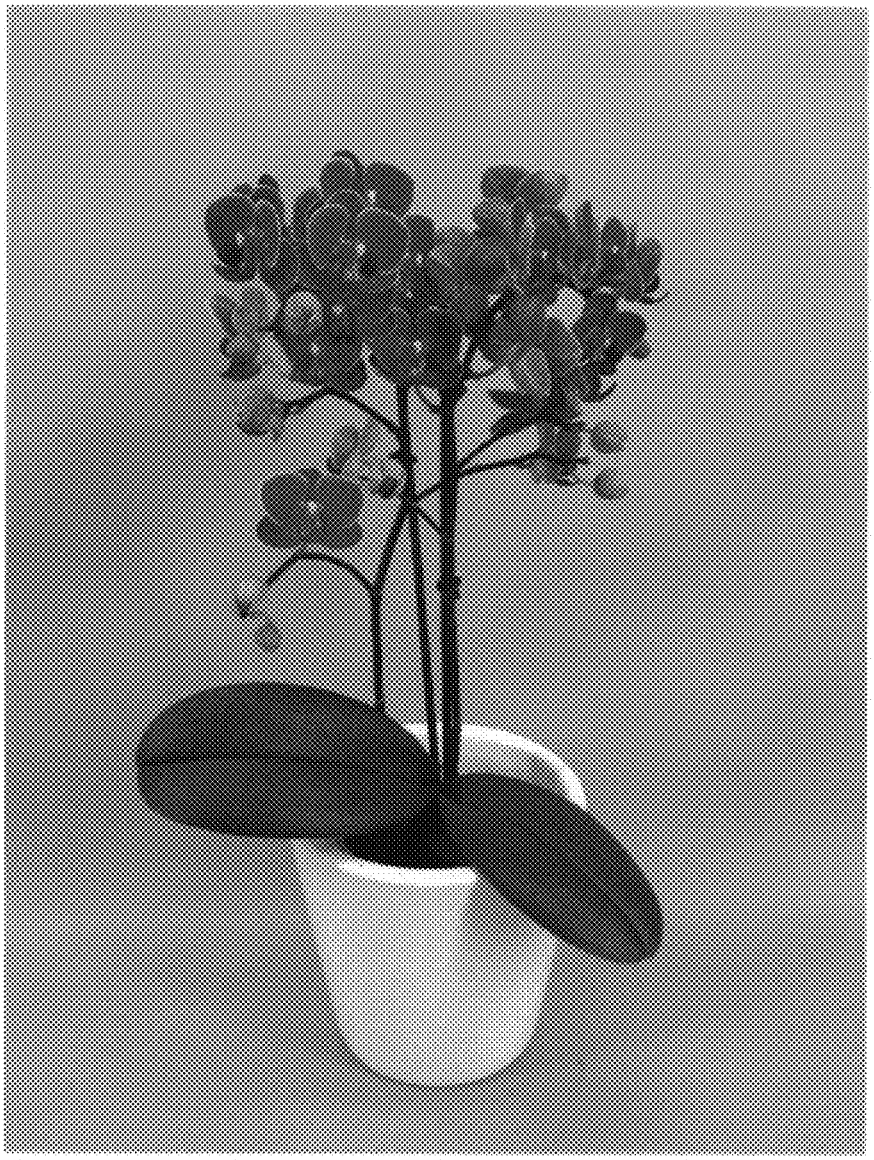
FIG. 1 shows the overall plant habit, including blooms, buds and foliage of 'PHALFEMYM'.
Figure 2:
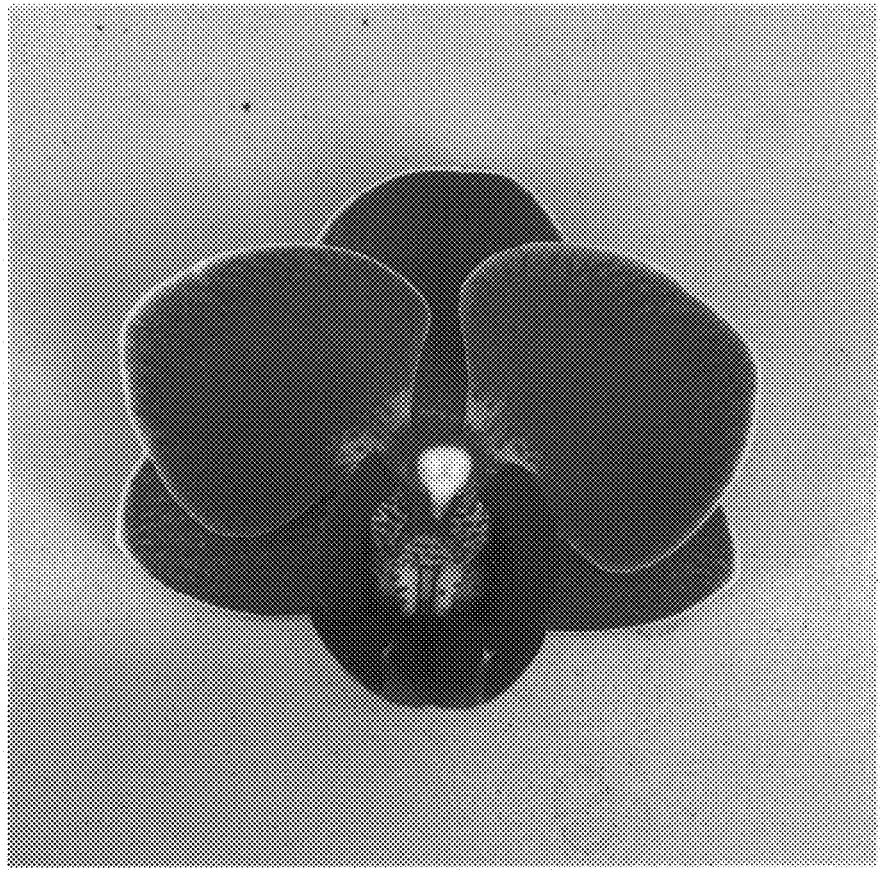
FIG. 2 shows a close-up of a flower of 'PHALFEMYM'.
Figure 3:
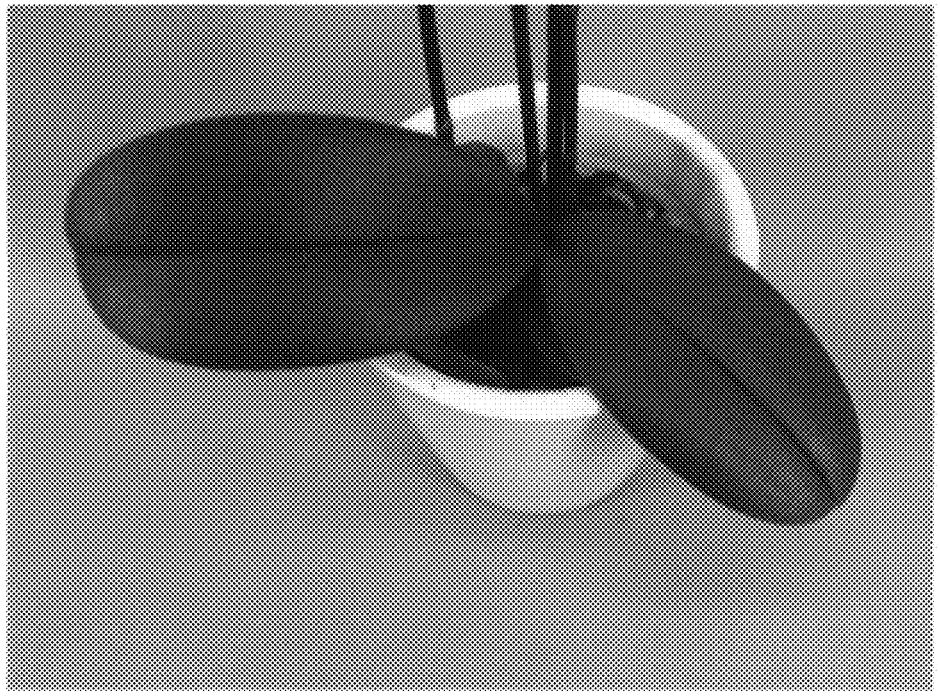
FIG. 3 shows a close-up of the leaves of 'PHALFEMYM'.

The following detailed description sets forth the distinctive characteristics of 'PHALFEMYM'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in March 2017 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFEMYM'.

Parentage:

*Female parent*.—*Phalaenopsis* cultivar '01-1787' (unpatented).

*Male parent*.—*Phalaenopsis* cultivar '01-1712' (unpatented).

Propagation:

*Type*.—Meristem tissue culture.

Roots:

*Root description*.—Greyed-green colored roots (between RHS 190B and 190C) with branching lateral roots having light green colored root tips (RHS 144C).

Plant:

*Commercial crop time to flowering*.—Approximately 48 to 50 weeks from a rooted cutting to finish in a 12 cm pot.

*Growth habit of peduncle*.—Upright to slightly pendant.

*Height (from soil level to top of inflorescence)*.—Approximately 33.0 cm to 38.0 cm.

*Width (measured from leaf tips)*.—About 25.0 cm to 27.0 cm.

*Vigor*.—Strong.

Leaves:

*Mature leaves*.—Quantity per plant: 6 to 9 leaves are produced before flowering. Length (fully expanded): 13.0 cm to 16.0 cm. Width: 7.0 cm to 7.5 cm. Shape: Oblong. Base shape: Moderately elongated. Apex: Rounded unequal. Arrangement: Alternate; half-up/horizontal and on two sides. Attachment: Leaves are directly attached to the stem. Leaf blade angle with the petiole (measured from the horizontal position): Between 10 degrees and 20 degrees. Leaf margin: Entire. Color: Upper surface: RHS 147A. Lower surface: RHS 147B. Texture: Smooth. Thickness: 2.2 mm to 2.5 mm. Venation: Pattern: Parallel. Color of the midvein: Upper surface: RHS 147A. Lower surface: RHS 147B.

Peduncle:

*Quantity per plant*.—1 to 3.

*Number of flowers per peduncle*.—16 to 21.

*Length*.—33.0 cm to 38.0 cm.

*Diameter*.—4.2 mm to 4.5 mm.

*Strength*.—Strong.

*Aspect*.—Upright to slightly pendant.

*Texture*.—Smooth.

*Color*.—Brown (RHS 200A).

*Internode length*.—40.0 mm to 50.0 mm.

*Callosities*.—None.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 180.0 mm to 220.0 mm.

*Flowering time*.—First flowers can be expected 10 to 11 months after planting in a 12 cm (diameter) pot.

*Flower*.—Height: 36.0 mm to 38.0 mm. Diameter: 42.0 mm to 44.0 mm. Depth of lip: 15.0 mm to 17.0 mm. Shape in lateral view: Concave. Rate of opening: Fully opened about 2-3 days after petal and sepal separation. Orientation at opening: Slanted upward and outward.

*Flower longevity*.—On the plant: 10 to 15 weeks.

*Fragrance*.—Absent.

*Flower bud*.—Average size: Medium. Length: 14.0 mm to 16.0 mm. Width: 12.0 mm to 14.0 mm. Shape: Egg shaped. Color: Green (between RHS 145B and 145C) at the base and purple (RHS N77B) toward the tip.

*Petals*.—Arrangement: Open/free. Number per flower: Three. Shape: Semi-circular. Apex: Obtuse asymmetric. Margin: Entire. Length (from base to tip): 20.0 mm to 22.0 mm. Width: 22.0 mm to 24.0 mm. Color (when fully opened): Upper surface: Basic color: Purple (RHS N78A). Over color: Light purple at the base (RHS 76B) and edge (RHS 76C). Lower surface: Basic color: Purple (RHS N78A). Over color: Purple (RHS N78B).

*Dorsal sepal*.—Shape: Rounded. Number per flower: One. Apex: Slightly emarginated symmetric. Margin: Entire. Length (from base to tip): 20.0 mm to 22.0 mm. Width: 18.0 mm to 20.0 mm. Texture (both upper and lower surfaces): Smooth and satiny. Color (when fully opened): Upper surface: Basic color: Purple (RHS N78A). Over color: Purple edge (RHS 76B/76C). Lower surface: Basic color: Purple (RHS N78B). Over color: Light purple (RHS N78D).

*Lateral sepals*.—Shape: Ovate. Number per flower: Two. Apex: Obtuse asymmetric. Margin: Entire. Length (from base to tip): 22.0 mm to 24.0 mm. Width: 18.0 mm to 20.0 mm. Texture (both upper and lower surfaces): Smooth and satiny. Color (when fully opened): Upper surface: Basic color: Purple (RHS N78A). Over color: Green at the base (RHS 145C); small red-purple dots at the base (RHS 71A). Lower surface: Basic color: Purple (RHS N78C). Over color: Light purple (RHS N78D) and at the base light green (RHS 145D).

*Labellum (lip)*.—Texture (both upper and lower surfaces): Smooth and satiny. Shape: Three-lobed with two prominent callosities at the central junction of the lateral lobes and base of the midlobe. Lateral lobes of labellum fold upward about the column; the midlobe extends forward and is terminated by two short filiform appendages at the apex. Whiskers: Present. Length of whiskers: 1.0 mm to 3.0 mm. Color of whiskers: Red-purple (RHS 71A). Pubescence on the lip: Absent.

*Lateral lobe*.—Shape: Weakly spatulate. Margin: Entire. Length: 12.0 mm to 14.0 mm. Width: 8.0 mm to 10.0 mm. Texture (both upper and lower surfaces): Smooth and satiny. Color: Dark red (RHS 187B) and slightly yellow at the base (RHS 8A); red-purple toward the edge (RHS 71A).

*Apical lobe*.—Shape: Ovate. Margin: Entire. Length: 15.0 mm to 17.0 mm. Width: 13.0 mm to 15.0 mm. Texture (both upper and lower surfaces): Smooth and satiny. Color: Red (RHS 60A) and red-purple (RHS 71A) toward the whiskers.

*Callus*.—Average size: Small. Height: 0.4 cm to 0.5 cm. Length: 0.4 cm to 0.5 cm. Width: 0.3 cm to 0.4 cm. Color: Yellow (RHS 8A) dotted (RHS 178A).

Reproductive organs:

*Column*.—Length: 7.0 mm to 9.0 mm. Diameter: 3.3 mm to 3.6 mm. Color: Purple (between RHS N78A and N78B).

*Pollinia*.—Quantity: 2. Diameter: 0.8 mm to 1.0 mm. Color: Orange (RHS 24A).

*Ovary*.—Length: 7.0 mm to 9.0 mm. Diameter: 1.3 mm to 1.5 mm. Color: Purple (RHS N78B).

*Pedicel*.—Length: 20.0 mm to 22.0 mm. Diameter: 1.4 mm to 1.6 mm. Texture: Smooth. Color: Green at the base (RHS 147C) and purple (RHS N78B) toward the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

Temperature tolerance: Tolerant to a low temperature of about 15° C. and to a high temperature of about 30° C.

COMPARISON WITH PARENTAL AND MOST SIMILAR VARIETIES

'PHALFEMYM' differs from female parent plant '01-1787' (unpatented) in that 'PHALFEMYM' has purple flowers with a center and edge pattern, and a red-purple lip with red-purple toward the whiskers, whereas '01-1787' has light purple flowers with a striped and edge pattern, and a red lip with purple toward the whiskers.

'PHALFEMYM' differs from male parent plant '01-1712' (unpatented) in that 'PHALFEMYM' has purple flowers with a center and edge pattern, and a red-purple lip with red-purple toward the whiskers, whereas '01-1712' has dark red-purple flowers with a center pattern, and a dark red lip.

'PHALFEMYM' is most similar to the commercial *Phalaenopsis* plants named 'PHALDIMXAP' (U.S. Plant Pat. No. 25,294) and 'PHALDYQ' (unpatented). 'PHALFEMYM' differs from the commercial variety 'PHALDIMXAP' in that 'PHALFEMYM' has flowers with a center and edge pattern, and a red apical lobe with red-purple toward the whiskers, whereas 'PHALFDIMXAP' has flowers with a center pattern, and a red, evenly colored apical lobe. Additionally, 'PHALFEMYM' has smaller flowers and narrower petals than 'PHALDIMXAP'.

'PHALFEMYM' differs from the commercial variety 'PHALDYQ' in that 'PHALFEMYM' has flowers with a center and edge pattern, and a red apical lobe with red-purple (RHS 71A) toward the whiskers, whereas 'PHALDYQ' has flowers with a striped and edged pattern, a red and red-purple (RHS N78A) apical lobe and no whiskers. Additionally, 'PHALFEMYM' has a wider dorsal sepal and wider petals than 'PHALDYQ'.

I claim:

1. A new and distinct variety of *Phalaenopsis* plant named 'PHALFEMYM', substantially as described and illustrated herein.

* * * * *